Figure 1A:
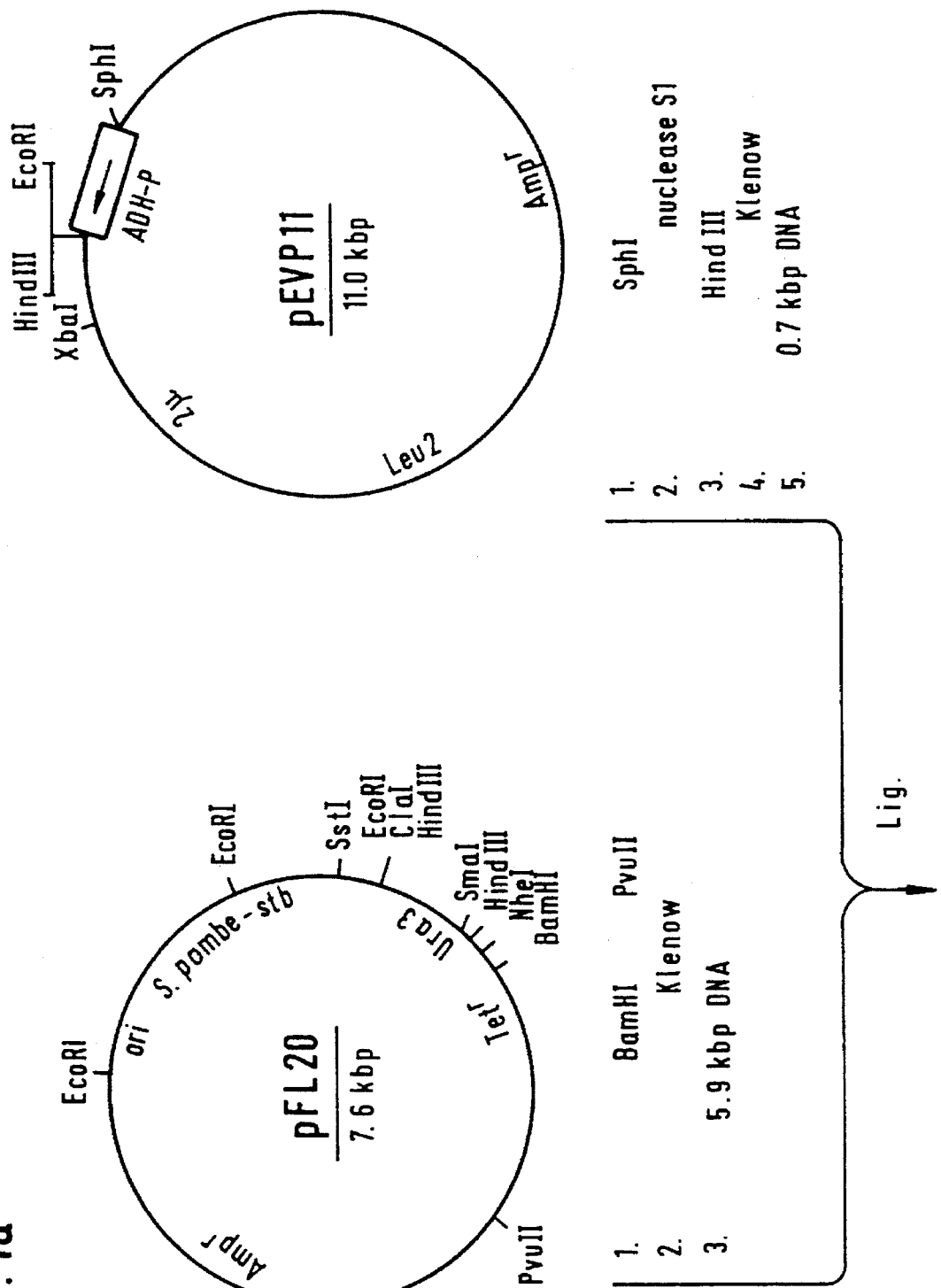

[19] United States Patent
Bröker

[11] Patent Number: 5,663,061
[45] Date of Patent: Sep. 2, 1997

[54] EXPRESSION VECTORS FOR THE SYNTHESIS OF PROTEINS IN THE FISSION YEAST SCHIZOSACCHAROMYCES POMBE

[75] Inventor: Michael Bröker, Marburg, Germany

[73] Assignee: Behringwerke Aktiengesellschaft, Marburg, Germany

[21] Appl. No.: 371,576

[22] Filed: Jan. 12, 1995

Related U.S. Application Data

[63] Continuation of Ser. No. 117,345, Sep. 7, 1993, abandoned, which is a continuation of Ser. No. 905,215, Jun. 29, 1992, abandoned, which is a continuation of Ser. No. 486,221, Feb. 28, 1990, abandoned.

[30] Foreign Application Priority Data

Mar. 2, 1989 [DE] Germany ............... 39 06 540.6

[51] Int. Cl.$^6$ ............... C12N 15/12; C12N 15/80; C12N 15/81
[52] U.S. Cl. ............... 435/69.6; 435/69.1; 435/172.3; 435/254.11; 435/254.2
[58] Field of Search ............... 435/69.6, 69.1, 435/217, 183, 172.3, 320.1, 254.2, 254.11

[56] References Cited

U.S. PATENT DOCUMENTS

| | | | |
|---|---|---|---|
| 4,929,553 | 5/1990 | Bussey et al. | 435/172.3 |
| 4,931,373 | 6/1990 | Kawasaki et al. | 435/69.2 |

FOREIGN PATENT DOCUMENTS

| | | |
|---|---|---|
| B-31454/84 | 2/1985 | Australia . |
| A-78694/87 | 3/1988 | Australia . |
| 0139383A1 | 5/1985 | European Pat. Off. . |
| 0268772A2 | 6/1988 | European Pat. Off. . |
| 0284044A1 | 9/1988 | European Pat. Off. . |

OTHER PUBLICATIONS

M.G. Lee and P. Nurse, Nature 327, 31–35 (1987).
D. Beach and P. Nurse, Nature 290:140–142 (1981).
R. Losson and F. Lacroute, Cell 32:371–377 (1983).
P.R. Russell, Nature 301:167–169 (1983).
M. Mertins and D. Gallwitz, Nuc. Acids Res. 15:7369–7379 (1987).
L. Guarente et al., Cell 20:543–553 (1980).
M. Broker, Biotechniques 5:516 and 518 (1987).
E. Amann et al., Gene 69:301–315 (1988).
Methods of Enzymatic Analysis 3rd Ed., H.U. Bergmeyer ed., Verlag Chemie, pp. 400–405 (1984).
M. Broker and O. Bauml, F.E.B.S. Letters 248:105–110 (1989).
M. Broker, BioTechniques 6:734 (1988).
Losson et al. Cell vol. 32:371–377 (1983).
Mertins et al. Nuc. Acid. Res. 15:7369 (1987).
Takahashi et al. PNAS vol. 83:8019 (1986).
Jackson et al. Biochemical Journal 251(3):931 (1988) Abstract Only.
Kaeufer et al. Nature 318: 78 (1985) cited & provided as BIOSIS Abstr. Acc#81042759.
ATCC catalogue of Bacteria, Phogis, & rDNA Vectors, p. 251, ATCC, 16th Ed., 1985.
United States Biochemical Corporation, Enzymes & Reagents for Molecular Biology, 1988, pp. 168–171.

*Primary Examiner*—John LeGuyader
*Attorney, Agent, or Firm*—Finnegan, Henderson, Farabow, Garrett & Dunner, L.L.P.

[57] ABSTRACT

Particularly suitable expression vectors for the synthesis of proteins in the fission yeast Schizosaccharomyces pombe (S. pombe) are described. These expression vectors are (in addition to other advantageous elements, equipped with a strong homologous promoter and terminator).

8 Claims, 5 Drawing Sheets

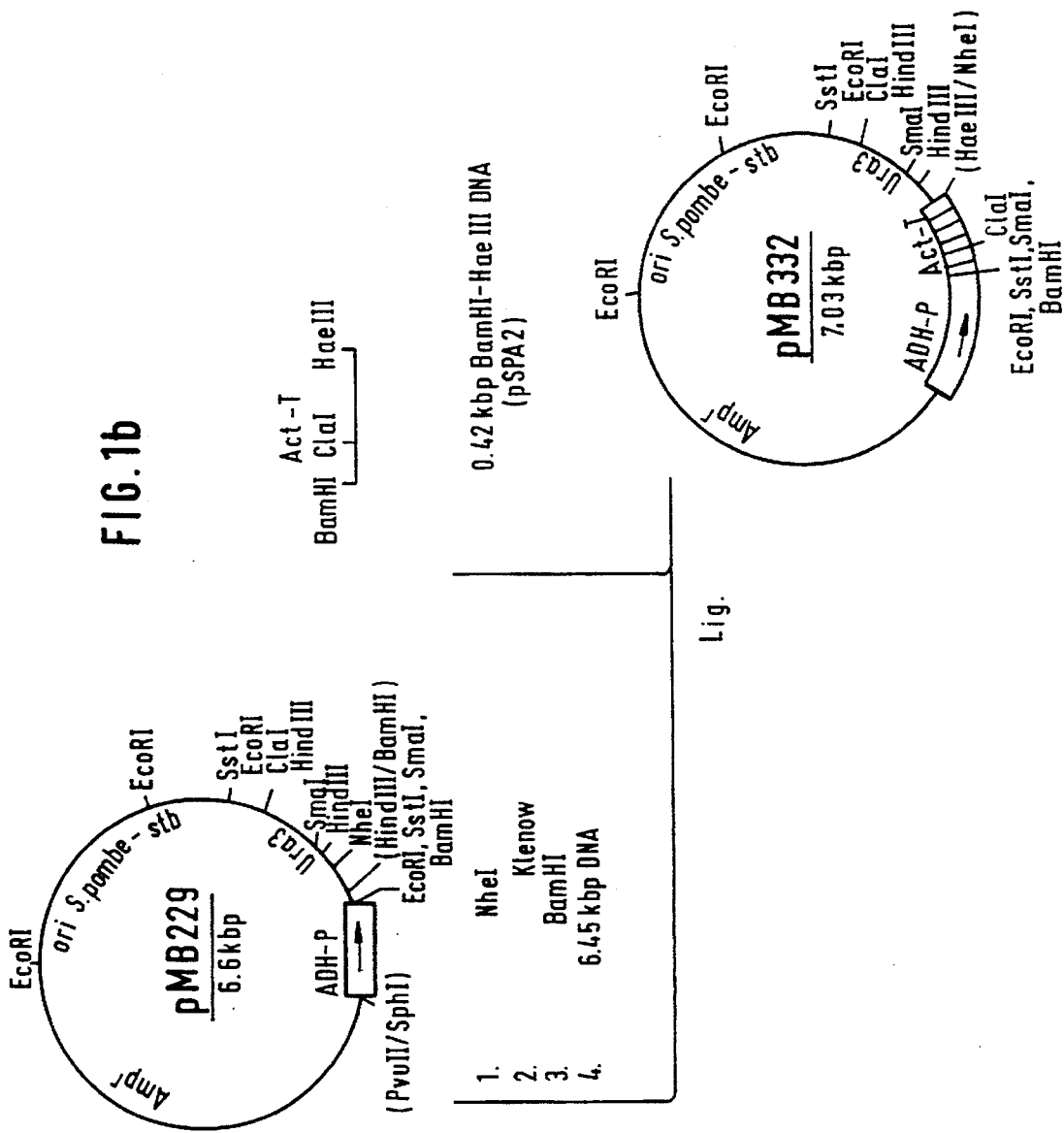

FIG. 2

ADH-P ←——→

```
                              -54
                               |
T T T A A G C A A G A G A A T T C G A G C T C G C C C C G G G T T T A A A
                              EcoRI    SstI        SmaI     DraI

A T G T C T G G A T C C A A G A T C T G G A T C C A G A C A T T T T T A A A A
        BamHI          BglII      BamHI                        DraI
```

EXPRESSION VECTORS FOR THE SYNTHESIS OF PROTEINS IN THE FISSION YEAST SCHIZOSACCHAROMYCES POMBE

This application is a continuation, of application Ser. No. 08/117,345, filed Sep. 7, 1993, abandoned, which is a continuation of application Ser. No. 07/905,215, filed Jun. 29, 1992, abandoned, which is a continuation of application Ser. No. 07/486,221, filed Feb. 28, 1990, abandoned.

The invention relates to particularly suitable expression vectors for the synthesis of proteins in the fission yeast Schizosaccharomyces pombe (S. pombe). These expression vectors are equipped with a strong homologous promoter, in addition to other advantageous elements.

Genetic engineering methods have made it possible to synthesize both homologous and heterologous proteins in large amounts in yeasts. Particular attention to date has been directed at baker's yeast Saccharomyces cerevisiae as host, because this was the first yeast for which vector systems and transformation methods were worked out. Expression systems have been worked out only recently for other yeasts such as, for example, representatives of the genera Kluyveromyces, Hansenula, Pichia and Schwannomyces, because less general knowledge of the classical and molecular genetics of these yeasts was available. There have to date been only a very few reports on the synthesis of heterologous proteins in the fission yeast S. pombe. S. pombe is one of the total of four species in the genus Schizosaccharomyces (Lindner). The other three species are: S. japonicus, S. malidovorans and S. octosporus. Only the species S. pombe has auxotrophic strains which permit genetic engineering work in analogy to baker's yeast.

S. pombe is, in terms of evolution, at a higher level than baker's yeast and in some respects has more resemblance to mammalian cells than to baker's yeast. Thus, for example, Lee and Nurse (Nature 327, (1987) pp 31–35) were able to identify the human gene which has homology with the cdc2 gene of S. pombe by complementation in this organism. The cell walls of baker's yeast are composed mainly of carbohydrates, especially of mannan and chitin. Apart from β-glucan (46–54%) and alpha-glucan (28%), fission yeasts also have, in contrast to baker's yeasts, galactomannan (9–14%) in the cell wall, specifically at the periphery of the cell wall and close to the plasmalemma. Galactomannan is composed of a (1–6)-linked backbone with (1–2)-linked mannose units and terminal galactose residues. The invertase of S. pombe is a glycoprotein which has terminal galactose units, whereas the carbohydrate portion of the invertase from baker's yeast is composed only of mannose. The ability of fission yeasts to synthesize more complex carbohydrates and glycoproteins than baker's yeast may be a crucial criterion for the biological activity, stability and antigenicity of recombinant proteins. Another advantage of S. pombe over baker's yeast in biotechnological processes may be the property that it is still able to grow at 37° C. –42° C. In order to be able to use a particular organism as host for the preparation of proteins by genetic manipulation, particular requirements must be met by the organism as well as the cloning vectors.

The following features are desirable:

1. The yeast strain should have one or more auxotrophic markers, preferably defects in the biosynthetic enzymes of amino-acid or purine-pyrimidine metabolism.
2. The vector should
   a) for autonomous replication have so-called origins of replication (ori) or autonomously replicating sequences (ars) both for the yeast and for a prokaryotic cell, preferably for E. coli
   b) have a strong promoter for initiating the desired mRNA transcription
   c) have a transcription terminator so that the expressed mRNA transcript has a defined length
   d) have unique restriction cleavage sites between the promoter and the terminator element for cloning in foreign DNA
   e) have a resistance gene for selection in bacteria (for example ampicillin resistance)
   f) have genes for complementation of the auxotrophic markers of the strain, which confer the appropriate prototrophy on the strain
   g) despite all the desired functions, not be too large because otherwise, for example, the transformation efficiency is too greatly diminished.

Of the criteria listed here, the host-specific properties are met by three S. pombe strains which have defects in the uracil or in the leucine or arginine metabolism. Thus, there is available a S. pombe strain which is deficient in orotidine-5'-phosphate decarboxylase (ura4). Another strain no longer synthesizes intact isopropylmalate dehydrogenase (Leu1). The ura4marker of S. pombe can be complemented by the corresponding ura3gene of S. cerevisiae, and the Leu1gene of S. pombe can be complemented by the Leu2gene of baker's yeast. An Arg7-1 S. pombe strain can be complemented by the cloned Arg7 gene which codes for argininosuccinate lyase.

Transformations of S. pombe with a plasmid (pDB248) were described for the first time by Beach and Nurse (Nature 290, (1981) pp 140–142). The vector constructed by them has an element which makes the plasmid capable of autonomous replication, but it emerged that this vector does not remain stably in the cells and is lost during mitotic segregation. Another vector (pFL20), which was developed by Losson and Lacroute (1983) Cell 32, 371–377, contains, in addition to the ars element, a DNA unit (stb) which results in the plasmid being passed on symmetrically to parent and daughter cell during mitosis. Whereas the vector pDB248 mediates leucine prototrophy in leu1 strains, the plasmid pFL20 confers the ability to synthesize uracil on ura4 strains. The particular mRNA transcripts are initiated by promoters of the baker's yeast genes in the fission yeast. These examples show that transcription start signals of baker's yeast function in fission yeast.

However, the transcription starts of baker's yeast genes are not identical to the corresponding sites in the homologous system in S. pombe (Russel, (1983) Nature 301, pp 167–169). There are likewise differences in transcription termination.

We have found that expression of foreign genes in S. pombe can be increased if promoters and terminators from S. pombe are used. This applies very generally to the use of homologous promoters and terminators in Schizosaccharomyces.

Accordingly, the invention preferably relates to vectors for the expression of foreign genes in S. pombe, these vectors containing a S. pombe promoter, preferably the promoter of the S. pombe alcohol dehydrogenase gene, and a S. pombe terminator, preferably of the S. pombe actin gene, in addition to other elements of a vector framework. These other elements are, individually or in combination, an antibiotic-resistance gene in E. coli, a replication origin in E. coli, a replication origin and the "stb" element for S. pombe and a complementing gene for the selected auxotrophy of the S. pombe host, preferably the Ura3 gene of S. cerevisiae for complementation of the ura4 defect of S. pombe, but also, for example, the Arg7 gene of S. pombe or the Leu2 gene of S. cerevisiae.

The invention is further disclosed in the Examples and the patent claims.

EXAMPLES

1. Vector construction

Figure 1C:
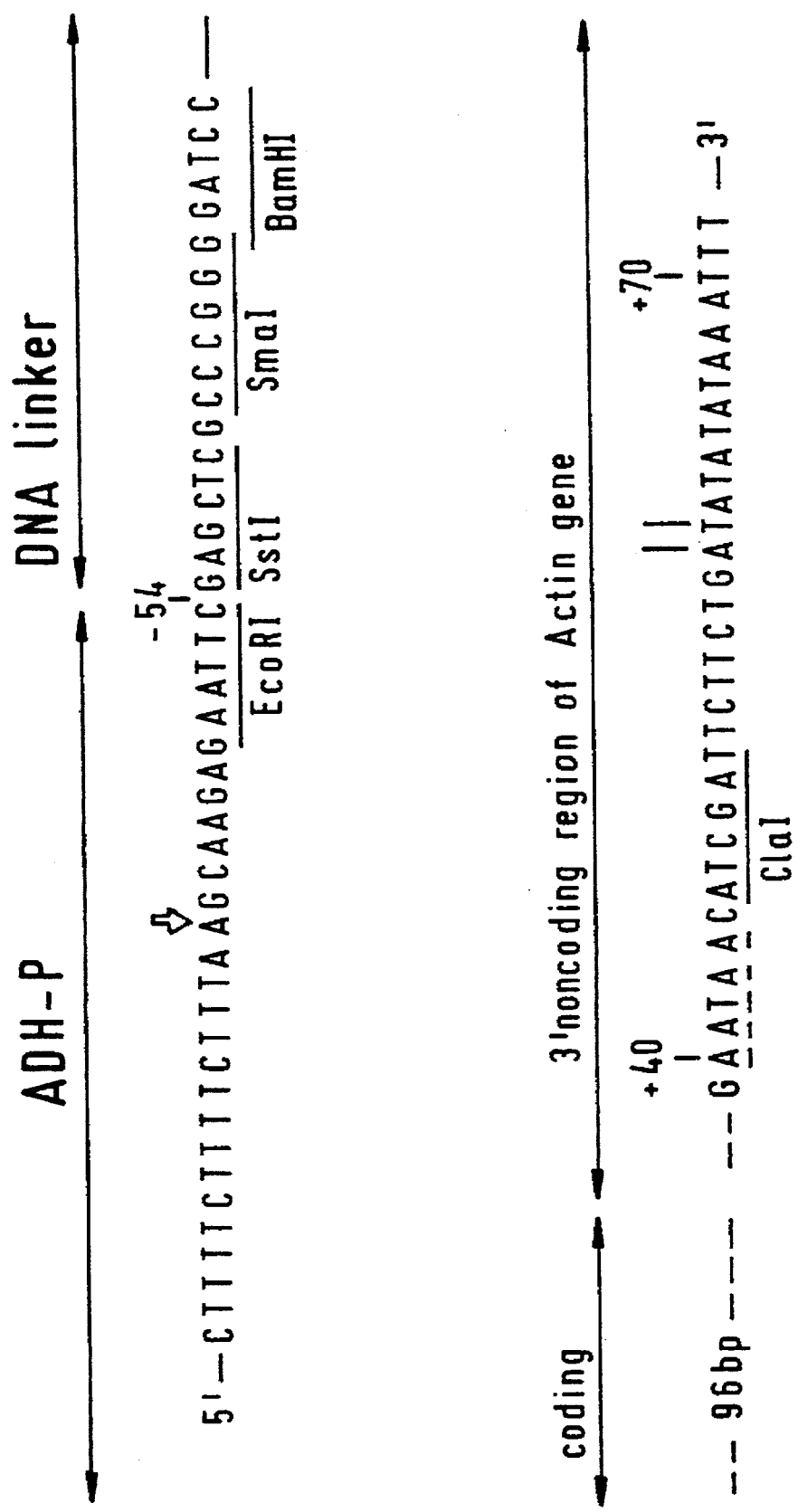
Figure 3:
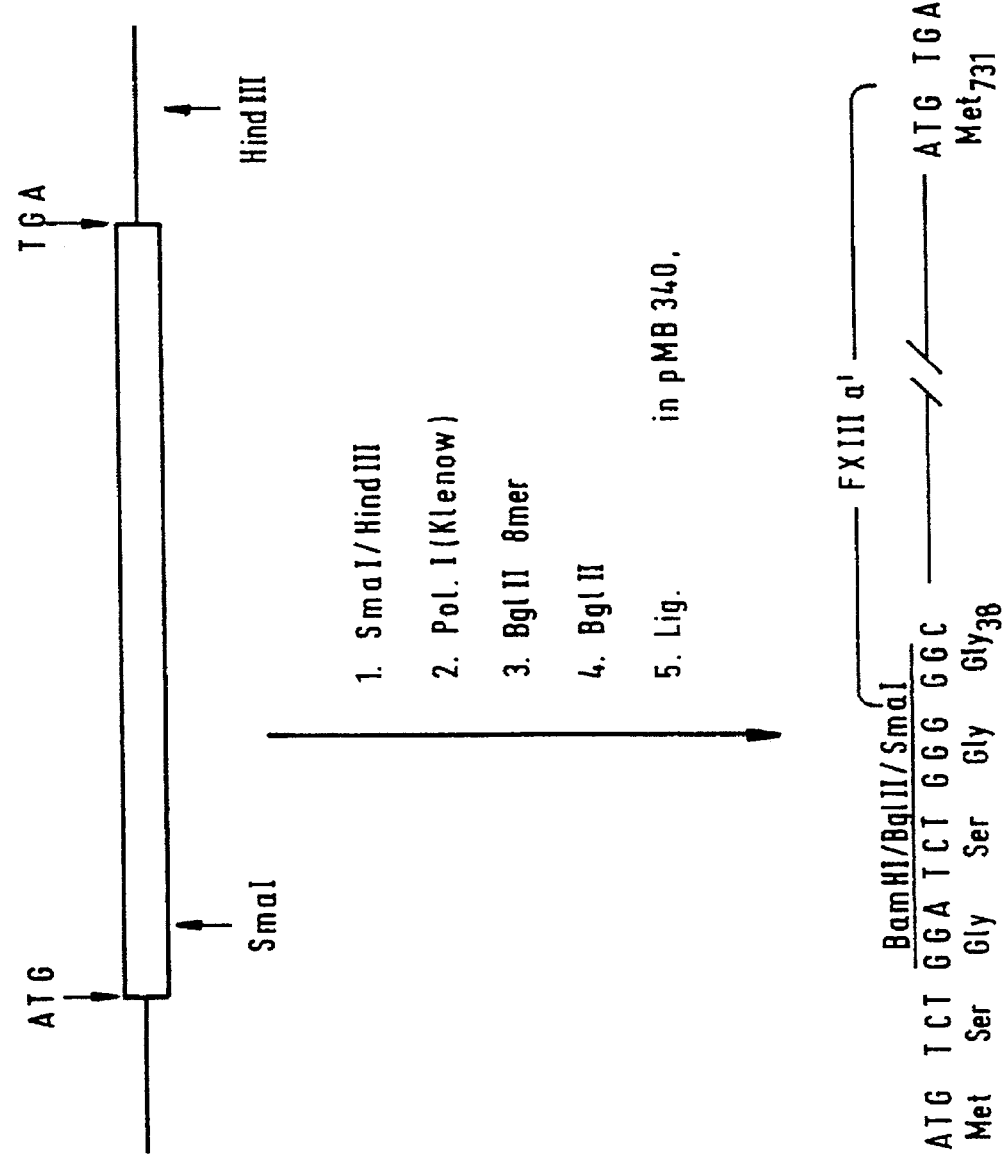

The vector pFL20 served as the basis for the mediation of ampicillin resistance in E. coli, of the "ori" function in E. coli, of the "ori" and the "stb" function in S. pombe and of the Ura3 gene of S. cerevisiae for complementation of the ura4 gene of S. pombe. The plasmid pFL20 was digested with BamHI and PvuII, the protruding 5' ends were filled in with polymerase (Klenow fragment) and the DNA fragment 5.9 kbp in size was isolated. The S. pombe alcohol dehydrogenase (ADH) gene control region (promoter) within which are located the recognition sites for initiation of transcription was cloned into this prepared vector which now no longer carries the original tetracycline-resistance gene. Used for this purpose was a DNA fragment which is 0.7 kbp in size, is located at the 5' end in front of the translation start signal of the ADH gene and terminates with the EcoRI site up to position −54 bp in front of the ATG start codon. The source used for the ADH promoter fragment was the SphI-HindIII a DNA fragment which is 0.7 kbp in size from the plasmid pEVP11 which in turn was produced by cloning the EcoRI-SphI DNA fragment which carries the S. pombe ADH promoter, together with the EcoRI-HindIII polylinker fragment from pUC12, into the S. cerevisiae-E. coli shuttle vector YEp13 after digestion with EcoRI and SphI (FIG. 1).

The new vector pMB229 which was produced has the advantage over the plasmid pEVP11 that 1. it is able to undergo stable autonomous replication in S. pombe, 2. non-essential DNA regions, such as coding regions of the E. coli tetracycline gene and of the S. cerevisiae 2 μDNA, have been deleted and 3. the vector is very small as a yeast vector, having about 6.6 kbp. The unique BamHI site towards the 3' end from the ADH promoter provides the opportunity of cloning in foreign genes and thus of placing the expression of the foreign gene under the control of the ADH promoter.

A transcription termination unit was inserted into the vector pMB229 towards the 3' end from the ADH promoter. For this, the BamHI-HaeIII DNA fragment, which is 0.42 kbp in size, of the S. pombe actin gene, which carries the transcription terminator, was isolated from the plasmid pSPA2 (Mettins and Gallwitz, Nucleic Acids Research 15, 7369–7379 (1987)) and cloned into pMB229. For this, pMB229 was first digested with NheI, the protruding 5' ends were filled in with polymerase I (Klenow), the plasmid was then digested with BamHI, and the DNA fragment which is 6.45 kbp in size was isolated and ligated with the DNA fragment which is 0.42 kbp in size from pSPA2. Hence the new plasmid pMB332 (FIG. 1) has a transcription initiation and termination unit from two different S. pombe genes, namely from the ADH gene and from the actin gene. Transcription in the ADH promoter portion should start 24 bp in front of the unique BamHI site, so that when a foreign gene is cloned in there is formation of a hybrid mRNA which carries portions from the ADH gene, from the DNA linker originally deriving from pUC12, and from the DNA which is cloned into the vector pMB332. There is no translation start codon between the transcription start and the BamHI site so that the first ATG triplet of the recombinant mRNA-can function as translation start. The signals for termination of transcription are located 8 bp towards the 3' end from the ClaI site. Termination in the actin gene is at bp +59 and +60. In the pMB332 vector, these termination stops are 117 and 118 bp towards the 3' end from the unique BamHI site so that there is on the recombinant mRNA a 3'-nontranslated region whose length depends on the foreign DNA which has been cloned in, unless efficient transcription stop signals are located on the foreign DNA which has been cloned in.

EXAMPLES 2 and 3

The applicability of the expression vector for the synthesis of foreign proteins in S. pombe was shown by a prokaryotic protein, beta-galactosidase (betagal) of E. coli, and a eukaryotic protein, human coagulation factor F XIIIa.

EXAMPLE 2 Synthesis of Beta-galactosidase

The plasmid pMB334 was prepared for the synthesis of betagal in S. pombe. The construction was carried out as follows: the betagal-encoding HindIII-NcoI DNA fragment which is about 3000 bp in size of the vector pLG400 (Guarente et al., Cell 20, (1980) 543–553) was treated with polymerase I Klenow fragment and cloned into the unique, likewise PolI-treated BamHI site of pMB332. In the new plasmid pMB334, the transcription of the betagal-encoding DNA is now under the control of the ADH promoter. The vector pMB334 was transformed into the uracil-auxotrophic strain S. pombe ura4-294 by the method of Broker (Biotechnigues 5, (1987) 516–518). In the assay designed by Miller, enzymatically active betagal was detectable in cell extracts from these transformants, and S. pombe (pMB334) colonies on agar nutrient media turn blue with the betagal indicator X-gal, whereas untransformed cells remain colorless.

EXAMPLE 3 Synthesis of Factor (F) XIIIa

The plasmid pMB333 was prepared for the synthesis of FXIIIa in S. pombe. The construction was carried out as follows: The EcoRI-HindIII DNA fragment, which is about 2400 bp in size and carries the cDNA for FXIIIa, of the vector pTrc99A-FXIIIa (Amann et al., Gene 69, 301–315, 1988) was treated with PolI and ligated into the unique, likewise PolI-treated BamHI site of the plasmid pMB332.

Transcription of the FXIIIa cDNA in the new plasmid is under the control of the ADH promoter. The vector pMB333 was transformed into S. pombe ura4-294. 2 mg/l FXIIIa were detectable with a specific ELISA in extracts of cells which had grown in a complex medium in shake cultures. The same concentration of FXIIIa was measured in the Karges activity assay (in: Methods in Enzymatic Analysis, Vol. 5, pp 400–405, (Bergmeyer, H. U. ed.), 1984). Western blot analyses were able to show that the FXIIIa from yeasts has the same migration behavior as placental FXIIIa and thus is of the same molecular weight.

EXAMPLE 4 Construction of a S. pombe "ATG Vector"

If the intention is to express protein fragments which have no amino-terminal methionine which is encoded by the translation start codon ATG, this signal can be provided by the vector. For this, the plasmid pMB332 was converted into a "ATG vector" (pMB340).

Subsequently, pMB332 was opened with BamHI, and the protruding DNA single strands were digested off with soybean S1 nuclease. Then an oligonucleotide which contains an ATG translation start signal was incorporated (see FIG. 2). The ATG codon is followed by a BamHI and a BglII site, into which the foreign DNA can be inserted, in such a manner that the protein-encoding sequence is in the reading frame having the ATG$_{Met}$ codon. The ATG triplet is immediately followed by a TCT codon which codes for serine. The intention of this is to ensure that the expressed protein has a long half-life; this is because many proteins which start with amino-terminal Met-Ser have a long half-life. The methionine is cleaved off such proteins by methionine aminopeptidase, and the serine is modified by a N-acetyltransferase. A primary translation product which is encodedby the vector pMB340 accordingly has the formula Met-Ser-polypeptide, it being possible for the recombinant protein to undergo post-translational modification into Ac-Ser-polypeptide.

It is subsequently possible for the DNA cloned into the vector pMB340 to be cut out with DraI and inserted into other vectors as cassette. In the transfer there is also transfer of the base-pair sequence AAA, which is located 5' in front of the ATG translation start codon, which has the advantage that an A is present in position −3 in front of the translation start on the mRNA, which brings about efficient translation. The vector pMB340 thus provides the possibility of efficient expression of any protein fragment in S. pombe, there being up to 2 to 6 additional amino acids at the amino terminus of the recombinant protein.

EXAMPLE 5 Expression of FXIIIa' With the Aid of the "ATG Vector" pMB340

FXIIIa is converted by thrombin into enzymatically active FXIIIa'. This entails cleavage of the amino-terminal peptide sequence (activation peptide) between Arg$_{37}$ and Gly$_{38}$. Within these thrombin cleavage sites there is at the cDNA level a unique SmaI cleavage site which can be used to cleave the coding cDNA region of FXIIIa' off the coding region of the activation peptide. Subsequently the FXIIIa cDNA was digested with SmaI and HindIII, the HindIII site was filled in by polymerase I Klenow in the presence of dNTPs, and a BglII 8mer linker (5'-CAGATCTG-3') was ligated onto the cDNA which now codes for FXIIIa'. After digestion with BglII, the FXIIIa'-specific cDNA was ligated into pMB340 linearized with BamHI. The new vector pMB357 thus codes for an FXIIIa which is already activated and which, provided for by the vector and the cloning procedure, has five additional amino acids at the amino terminus.

This modified FXIIIa' synthesized in S. pombe had transglutamina activity even without thrombin activation.

These examples demonstrate that it is possible to prepare foreign prokaryotic and eukaryotic proteins in active form in S. pombe with the aid of the new expression plasmids pMB332 and pMB340 which have been produced. It is subsequently possible to insert additional restriction sites towards the 3' end from the ADH promoter in order, for example, to allow foreign DNA to be ligated in directed orientation. Insertion of a DNA sequence with the ATG base sequence can be used to provide a signal for the initiation of translation, and thus also to bring about the expression of gene fragments without this own translation start signal. Since the half-life of the foreign protein and post-translational modifications may be strain-dependent, it is possible, by replacing the ura marker in the plasmid pMB332 by, for example, the Leu2 marker or Arg7 marker, to modify the expression vector in such a way that Leu2 or Arg7 auxotrophic strains of S. pombe can also be transformed.

Plasmids pMB332 and pMB340 are deposited in the permanent culture collection of the Deutsche Sammlung yon Mikroorganismen und Zellkuturen GmbH (DSM) in Braunschweig, Germany. The accession numbers for the deposited plasmids are DSM 9489 and DMS 9490, respectively. The deposit was made on Oct. 7, 1994.

I claim:

1. The expression vector pMB332.
2. A process for the preparation of a foreign protein comprising the steps of
   a. cloning DNA encoding said foreign protein into the vector as claimed in claim 1,
   b. transforming said vector into Schizosaccharomyces cells,
   c. expressing said foreign protein, and
   d. isolating said foreign protein.
3. The process as claimed in claim 2 for the preparation of Factor XIIIa.
4. The process as claimed in claim 2 for the preparation of Factor XIIIa'.
5. The ATG expression vector pMB340.
6. A process for the preparation of a foreign protein comprising the steps of
   a. cloning DNA encoding said foreign protein into the vector as claimed in claim 5,
   b. transforming said vector into Schizosaccharomyces cells,
   c. expressing said foreign protein, and
   d. isolating said foreign protein.
7. The process as claimed in claim 6 for the preparation of Factor XIIIa.
8. The process as claimed in claim 6 for the preparation of Factor XIIIa'.

* * * * *